United States Patent [19]

Moon

[11] Patent Number: 5,914,092
[45] Date of Patent: Jun. 22, 1999

[54] FERMENTATION TANK SAMPLE VALVE STEAM STERILIZATION APPARATUS

[75] Inventor: Willard K. Moon, Groton, Conn.

[73] Assignee: Pfizer Inc., New York, N.Y.

[21] Appl. No.: 08/740,284

[22] Filed: Oct. 25, 1996

Related U.S. Application Data

[60] Provisional application No. 60/008,132, Oct. 31, 1995.
[51] Int. Cl.[6] .............................. C12M 1/02; A61L 2/00
[52] U.S. Cl. ......................... 422/295; 422/110; 422/292; 422/103; 435/283.1; 435/309.2; 73/863.86
[58] Field of Search .................................. 435/309.2, 30, 435/283.1; 422/101, 102, 295, 103, 99, 110, 292; 137/238; 96/223

[56] References Cited

U.S. PATENT DOCUMENTS 5,525,301  6/1996  Newberg et al. ...................... 422/99

*Primary Examiner*—Ponnathapura Achutamurthy
*Assistant Examiner*—P. Ponnaluri
*Attorney, Agent, or Firm*—Peter C. Richardson; Gregg C. Benson; A. Dean Olson

[57] ABSTRACT

An apparatus for maintaining the sterilization of a reactor vessel output. The apparatus comprises a connect means for connecting to and enclosing the reactor vessel output and a steam trap means for maintaining steam pressure. The steam trap means is in fluid communication with and downstream from both the connect means and an output means for releasing pressure. The output means is in fluid communication with and downstream from the connect means and the output means is upstream from the steam trap means. This apparatus provides a significant improvement to the fermentation industry by facilitating the maintenance of a sanitized sampling output.

1 Claim, 3 Drawing Sheets

FERMENTATION TANK SAMPLE VALVE STEAM STERILIZATION APPARATUS

This application claims the benefit of U.S. Provisional Application No. 60/008,132 filed on Oct. 31, 1995.

BACKGROUND OF THE INVENTION

This invention relates to the chemical processing industry, more particularly the fermentation industry and most particularly fermentation tank sampling apparatuses.

In the fermentation industry there is a requirement for maintaining sterile conditions to avoid contamination of the product by, for example, undesired microorganisms. The sterilization requirement applies to fermentation feed lines, water lines and even the sampling valves. Sampling valves are merely output valves connected to fermentation tank useful for taking samples in order to follow the progress of the fermentation reaction.

Although a sterilizing steam line is connected to a sampling valve, maintaining sterile sampling valves is particularly difficult. When the valve is closed the outside of the end of the valve (which may have a further nipple attached) is not in contact with the sterilizing steam. Alternatively, when the valve is open the reduction in pressure lowers the steam temperature to sub-optimum levels (e.g., 250° F. (121° C.) to 210° F. (99° C.). Typically, the sampling valves are left open to continuously bleed steam in an effort to maintain as sterile conditions as possible at the sample valve. These open sample valves (essentially open steam lines) result in a wasteful release of steam. The continuous steam venting also compromises work conditions. Finally, the steam venting results in a continuous dripping of condensate that can compromise working conditions.

Thus, there is a continuing need and a continuing search in this field of art for alternative fermentation tank sampling valve apparatuses.

SUMMARY OF THE INVENTION

This invention is directed to an apparatus for maintaining the sterilization of a reactor vessel output.

The apparatus comprises a connect means for connecting to and enclosing the reactor vessel output and a steam trap means for maintaining steam pressure. The steam trap means is in fluid communication with and downstream from both the connect means and an output means for releasing pressure. The output means is in fluid communication with and downstream from the connect means and the output means is upstream from the steam trap means.

This apparatus provides a significant improvement to the fermentation industry by facilitating the maintenance of a sanitized sampling output in addition to eliminating condensate spillage on floors, eliminating wasteful steam venting, reducing noise and increasing visibility.

Other features and advantages will be apparent from the specification and claims and from the accompanying drawings which illustrate embodiments of the invention.

DETAILED DESCRIPTION OF THE INVENTION

Figure 1:
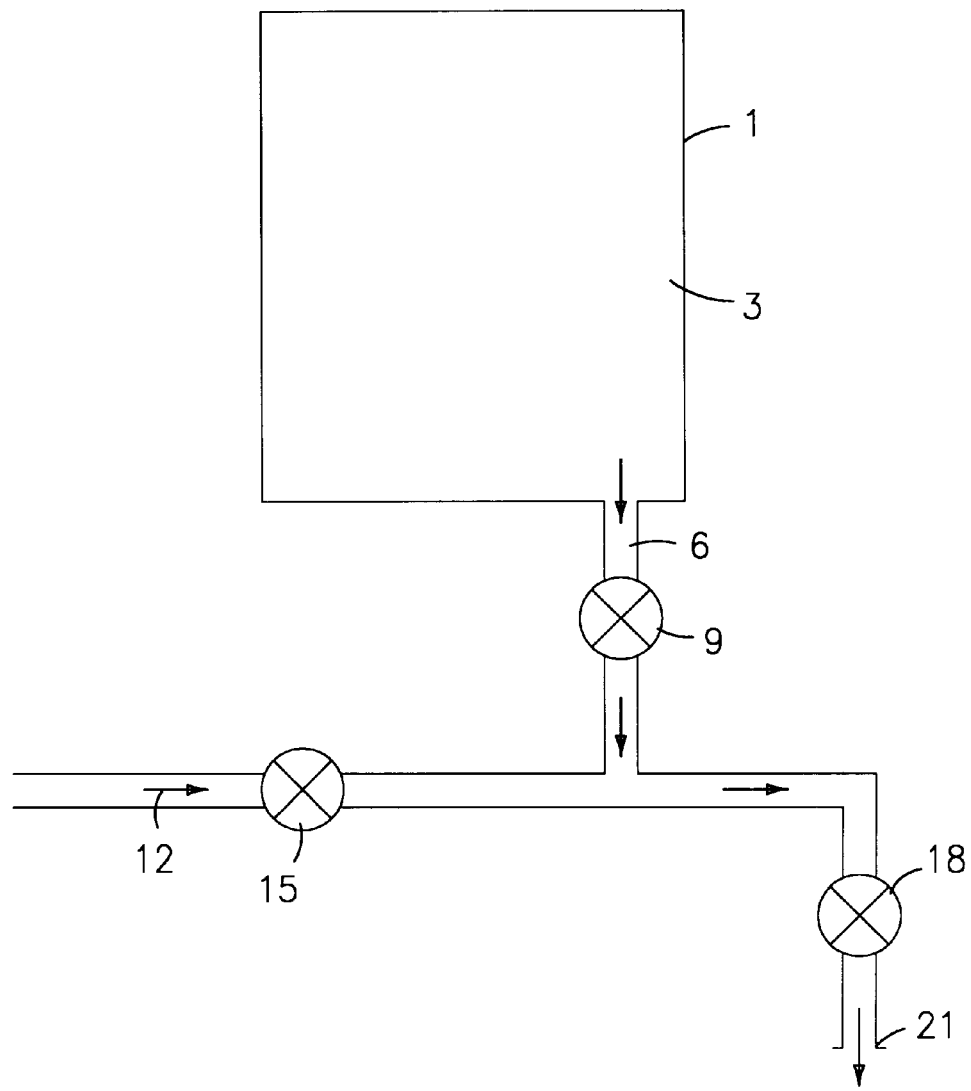
FIG. 1 is a schematic view of a fermentation tank, a steam line and output line.

According to FIG. 1 reactor vessel (e.g., fermentor vessel) 1 contains reaction fluid (e.g., fermentation fluid) 3. Fermentation vessel output 6 provides for fluid communication from fermentation vessel 1 to output tank valve 9 in a downstream direction. Output tank valve 9 provides for the control of the downstream flow through output 6. Steam line 12 provides for a source of steam and is in fluid communication with output 6. Steam control valve 15 provides for control of flow through steam line 12. Sampling valve 18 provides for the control of fluid communication with the external environment 22 through the end of the sampling assembly 21.

Figure 2:
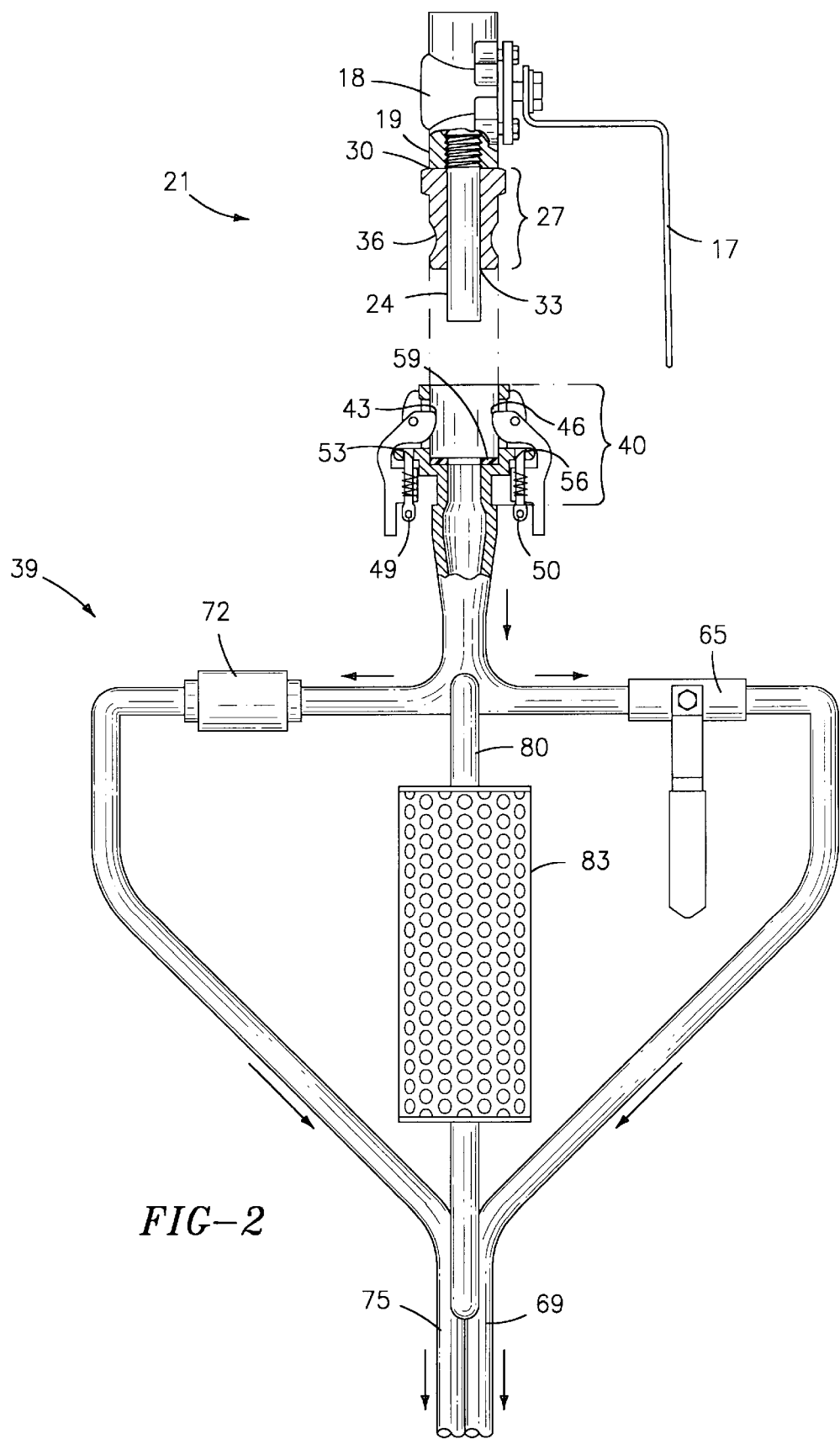
FIG. 2 is a top view of the sterilization apparatus of this invention in two parts, each partly in section.

According to FIG. 2 the sterilizing apparatus of this invention comprises two assemblies. The first is the sampling assembly 21 and the second is the sterilizing assembly 39.

The sampling assembly 21 comprises a tube such as a threaded pipe nipple 24 (fermentor vessel output) that is threaded into pipe 19 (which is typically part of the valve 18). In addition, a male connect means (e.g., male connector 27) is slid over the pipe nipple 24 and welded at point 30 to the pipe 19 and at point 33 to the pipe nipple 24. Alternatively, the male connector 27 may be welded to a washer, the male connector 27 welded to the pipe nipple 24 and the male connector 27 and pipe nipple 24 merely threaded into the pipe 19 (allowing for removal of the male connector 27). The male connector 27 has a recessed region 36 for receiving cams in order to lock the male and female connectors together at a joint area that is upstream of the nipple 24. Also, valve 18 controls the fluid flow and is actuated by handle 17.

The sterilizing assembly 39 is also depicted in FIG. 2 and includes connect means (female connect means) for connecting to and enclosing the nipple 24 and male connector 27 (fermentor vessel output). The female connect means includes a clamping means for clamping the female connect means to the male connect means. For example, a female connector 40 is sized to receive the male connector 27 so that cams 43 and 46 mate with the male connector recessed region 36. The cams 43,46 have spring loaded locking pins 49,50 that engage female connector extensions 53,56. In one cam position the pins springably engage female connector extensions 53,56 and the cams are locked so that they extend within the throat of the female connector portion 40. When the female connector 40 is mated with the male connector 27 the cams 43,46 are locked into the male connector recessed region 36 fastening the two connectors together. A rubber O-ring 59 (gasket) is seated at the bottom of female connector portion 40. When the two connectors are joined, the O-ring 59 seats against the bottom of male connector 27 at the weld point 33 forming an air tight compression seal. Exemplary male and female connectors 27, 40 are Civacon Locking Kamloks (OPW Co., Cincinnati, Ohio). The sterilizing assembly 39 has output means for controllably releasing pressure such as a pressure release valve 65 and outlet 69 (e.g., bypass valve). The pressure release valve 65 and outlet 69 is upstream of a steam trap means for maintaining steam pressure. The bypass valve allows for release of pressure from the steam trap so that the sterilizing assembly may be removed. An exemplary steam trap means is a steam trap 72 that is upstream of a condensate outlet 75. The steam trap 72 allows condensate to pass downstream at a predetermined temperature and pressure. An exemplary thermostatic bellows, steam trap is available from Spirax Sarco Inc.

(Allentown, Pa.) (for example a 0.5 inch TSS 300® Sealed Thermostatic Steam Trap) Steam traps are described in Papamarcos, John, SPECIAL REPORT, Steam Traps, PLANT SERVICES, October 1988, pp. 58–65. A handle 80 may be attached to the sterilizing apparatus 39 for ease of attachment. Preferably, the handle is heat shielded by for example, attachment to a porous metal shield 83 that may be gripped.

According to FIGS. 1 and 2, during use, the sterilizing assembly 39 encloses or covers the nipple 24 (the nipple 24 extends within the throat of the female connector) of the sampling assembly 21 and thus provides for sterilization of the nipple 24. The steam control valve 15 may be left open to continually bathe the sampling nipple 24 in steam or the steam control valve 15 may be opened for a time sufficient to sanitize the sampling nipple 24 prior to sampling. Thus, during operation the output tank valve 9 is closed and the steam control valve 15 is open. The pressure release valve 65 on the sterilizing assembly 39 apparatus is closed and sampling valve 18 is opened. This maintains a constant bath of pressurized sanitizing steam surrounding the sampling nipple 24. A sample of the fermentation fluid 3 may be taken from fermentor vessel 1 by first closing the steam control valve 15 and sampling valve 18. Then the pressure release valve 65 is opened. The female connector 40 is released from the male connector 27 and the sterilizing assembly 39 is released. The sample is taken by opening the sampling valve 18 and the output tank valve 9 for a sufficient time to obtain the desired sample size through the sterilized sampling nipple 24.

Subsequent to sampling, the sampling nipple 24 may be resterilized by closing 15 the output tank valve 9, fully draining any sample remaining down stream from the output tank valve 9 and opening steam control valve 15 to flush the lines with steam. These procedures are followed by closing steam control valve 15, reattaching the sterilizing assembly 39 to the sampling assembly 21, closing the pressure release valve 65 and opening the steam control valve 15 and sampling valve 18.

Figure 3:
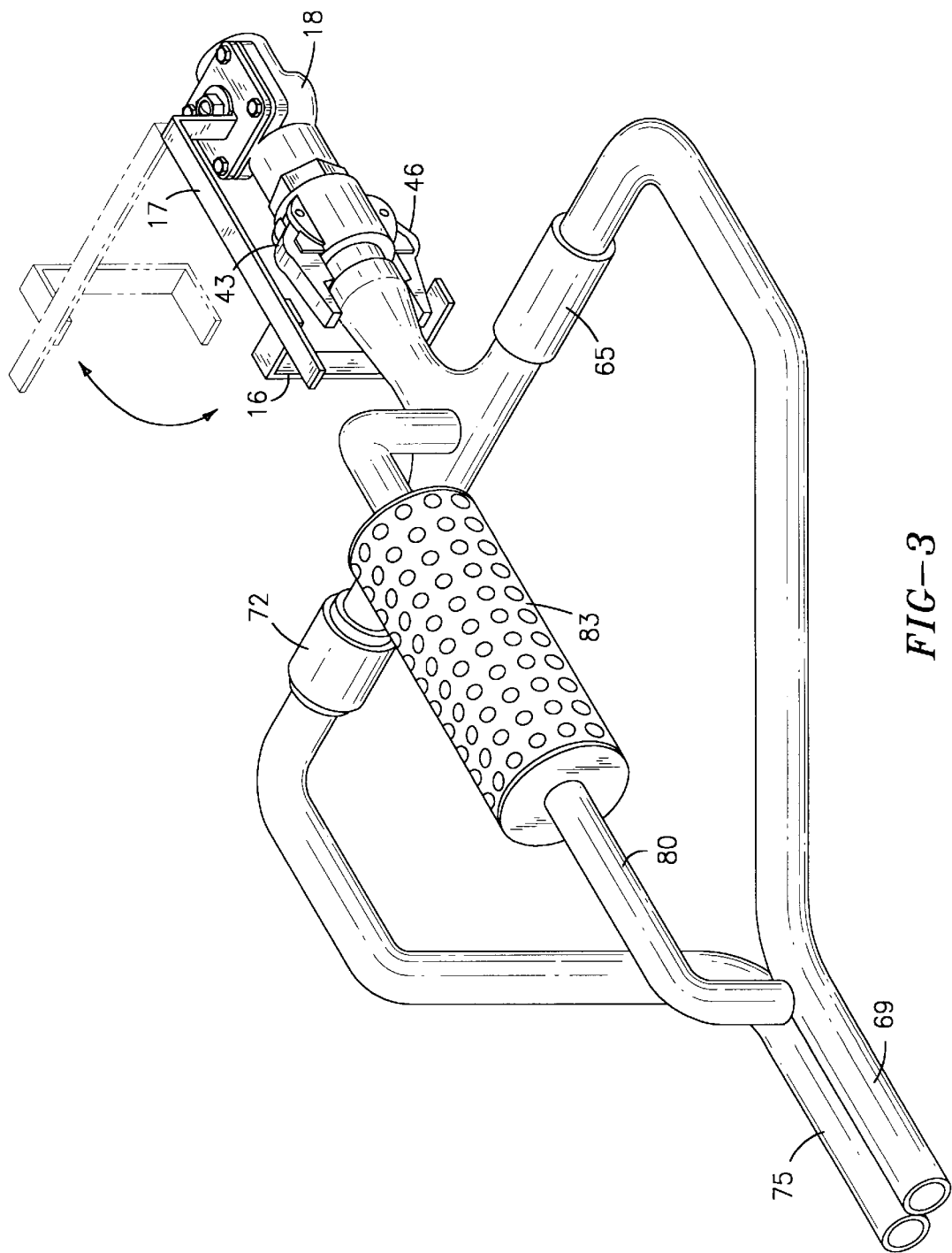
FIG. 3 is a perspective view of the sterilization apparatus of this invention.

FIG. 3 displays a further safety aspect of this invention. Handle 17 is connected to sampling valve 18 enabling control of the fluid flow through sampling valve 18 via a turn of the handle (e.g., a ninety degree turn as depicted in phantom). In the open valve position, handle 17 covers cam 43 thus providing a redundant restraining mechanism so that cam 43 cannot be opened and the sterilizing assembly 39 removed until the sampling valve 18 is closed. Analogously, handle 17 has an extension arm 16 that extends to cover cam 46 so that cam 43 cannot open accidentally. When a sample is required handle 17 is rotated to the closed position. Thus, the handle 17 and extension arm 16 are rotated from the position covering cams 43 and 46 enabling their releasing action and the separation of the sterilizing assembly 39 from the sampling valve end 20.

Prior to the use of this apparatus steam venting through the sampling valve 18 could maintain a temperature that was sub-optimal due to the lack of pressure at the vent. Accordingly, steam was continually vented in an effort to maintain the optimum of sanitary conditions at the nipple 24 of the sampling assembly 21. The apparatus of this invention facilitates the maintenance of a sanitized sampling output in addition to eliminating condensate spillage on floors, eliminating wasteful steam venting, reducing noise and increasing visibility.

It should be understood that the invention is not limited to the particular embodiments shown and described herein, but that various changes and modifications may be made without departing from the spirit and scope of this novel concept as defined by the following claims.

I claim:

1. An apparatus for the sterilization of a reactor vessel output comprising:
   a. female connect means for connecting to and enclosing the reactor vessel output;
   b. a sampling assembly comprising a male connector to join said female connect means wherein said female connect means is mated at a joint area with the male connector, a tube extending from said male connector downstream of said joint area and said female connect means including a clamping means for clamping said female connect means to said male connector;
   c. steam trap means for maintaining steam pressure, said steam trap means in fluid communication with said female connect means and said stream trap means disposed downstream from said female connect means, wherein said steam trap allows predetermined pressure, temperature and condensate to pass down stream;
   d. output means for controllably releasing pressure, said output means in fluid communication with said female connect means, and said output means disposed downstream from said female connect means and said output means upstream from said steam trap means; and
   e. a valve for controlling fluid flow through said reactor vessel output and handle means for controlling said valve, said valve disposed upstream of said output and said handle means disposed to block said clamping means from releasing said male connector from said female connect means when said valve is open.

* * * * *